United States Patent [19]

Nichols et al.

[11] Patent Number: 5,346,075
[45] Date of Patent: Sep. 13, 1994

[54] APPARATUS AND METHOD FOR HOLDING A MEDICAL INSTRUMENT

[75] Inventors: Robert L. Nichols, Jacksonville; Keith F. Lindsey, Troup; William H. Patterson, Jacksonville, all of Tex.

[73] Assignee: Johnson & Johnson Medical, Inc., Arlington, Tex.

[21] Appl. No.: 870,558

[22] Filed: Apr. 17, 1992

[51] Int. Cl.⁵ ............................................. A61L 2/00
[52] U.S. Cl. .................. 211/60.1; 211/70.6; 206/363; 422/300
[58] Field of Search ............... 211/70.6, 60.1; 422/300; 206/363, 364, 366, 369, 565

[56] References Cited

U.S. PATENT DOCUMENTS

| | | | |
|---|---|---|---|
| 4,043,754 | 8/1977 | Sklar | 206/565 X |
| 4,798,292 | 1/1989 | Hauze | 206/363 X |
| 4,854,475 | 8/1989 | Riihimaki et al. | 206/369 X |
| 4,915,918 | 4/1990 | Nichols | 206/363 X |
| 5,011,718 | 4/1991 | Patterson | 206/363 X |
| 5,080,874 | 1/1992 | Nichols | 206/363 X |
| 5,183,643 | 2/1993 | Nichols | 206/363 X |
| 5,202,098 | 4/1993 | Nichols | 206/363 X |

FOREIGN PATENT DOCUMENTS 2412465  8/1979  France ................. 206/565

OTHER PUBLICATIONS

"Middle Ear Instrument Protection and Sterilizing System", Micromedics, Inc., 268 E. Lafayette Frontage Rd., St. Paul, Minnesota 55107.
"module layout in basket", Jan. 1987, Micromedics, Inc. 268 E. Lafayette Frontage Rd., St. Paul, Minnesota 55107.
"Introducing Hold-Its", Micromedics, Inc., 268 E. Lafayette Frontage Rd., St. Paul, Minnesota 55107.
"Steril Container System", Aescullap, 875 Stanton Rd., Burlingame, Calif. 94010.
"Surgical Instrument Catalog", 4th Ed., 1988, Walter Lorenz Surgical Instruments, Inc., 9850 Interstate Center Dr., Jacksonville, Fla. 32218, pp. 935, 940 and 942.
"Wire Routing", 1990, Richco Plastic Company, 5825 N. Trip Ave., Chicago, Ill. 60646.
"Play It Safe with Instru-Safe TM Trays for Laparoscopic Surgery", Micromedics, Inc., 268 E. Lafayette Frontage Rd., St. Paul, Minnesota 55107.
"Instru-Safe TM Arthroscope Tray", Micromedics, Inc., 268 E. Lafayette Frontage Rd., St. Paul, Minnesota 55107.
"Rack-It", 1990, Vengo Industries Inc., 10119 Colonial Industrial Cr., South Lyon, Mich. 48178.

*Primary Examiner*—Robert W. Gibson, Jr.
*Attorney, Agent, or Firm*—Baker & Botts

[57] ABSTRACT

A method and apparatus are provided for holding a medical instrument. The medical instrument is held in a cradle (112) having first and second interlockable regions (114, 116). The cradle (112) is coupled to a first mating element (124). The first mating element (124) is coupled to a second mating element (126) through a selected aperture (128) of a platform (16), such that the cradle (112) is coupled to the platform (16). The platform (16) has multiple apertures (128, 130, 138).

54 Claims, 9 Drawing Sheets

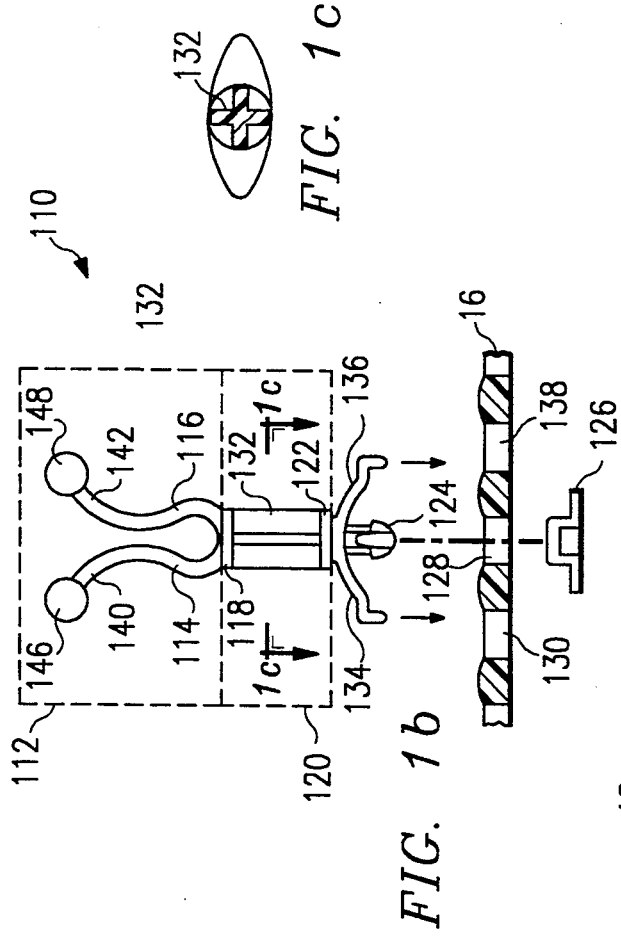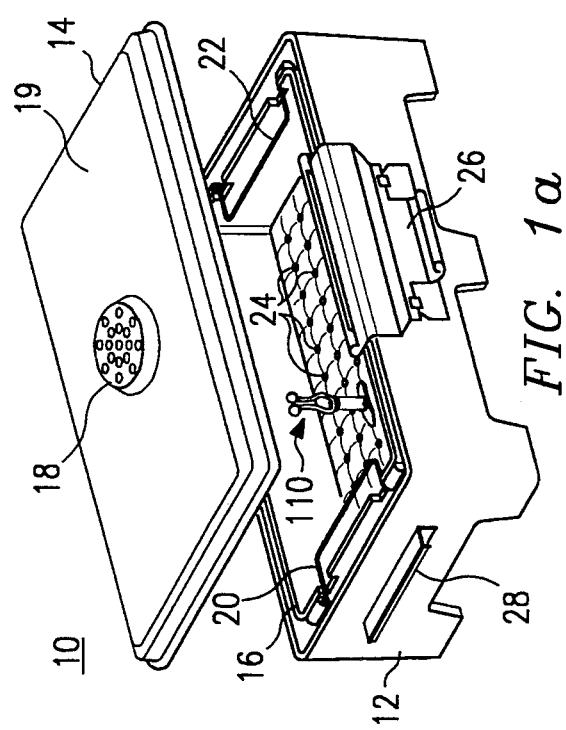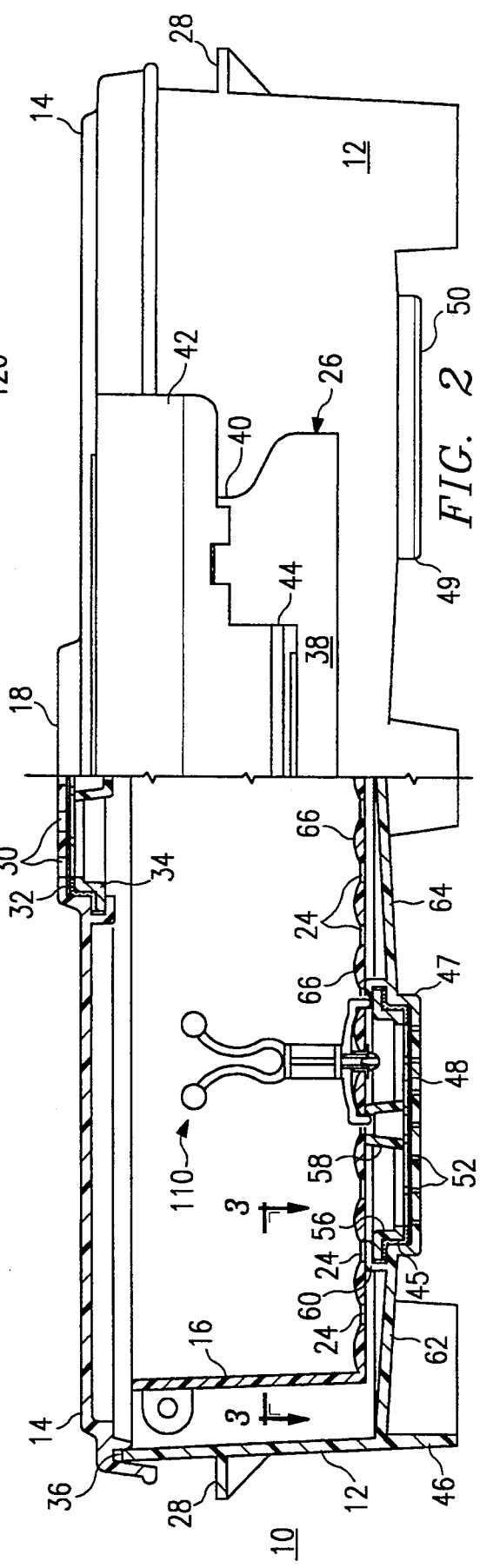

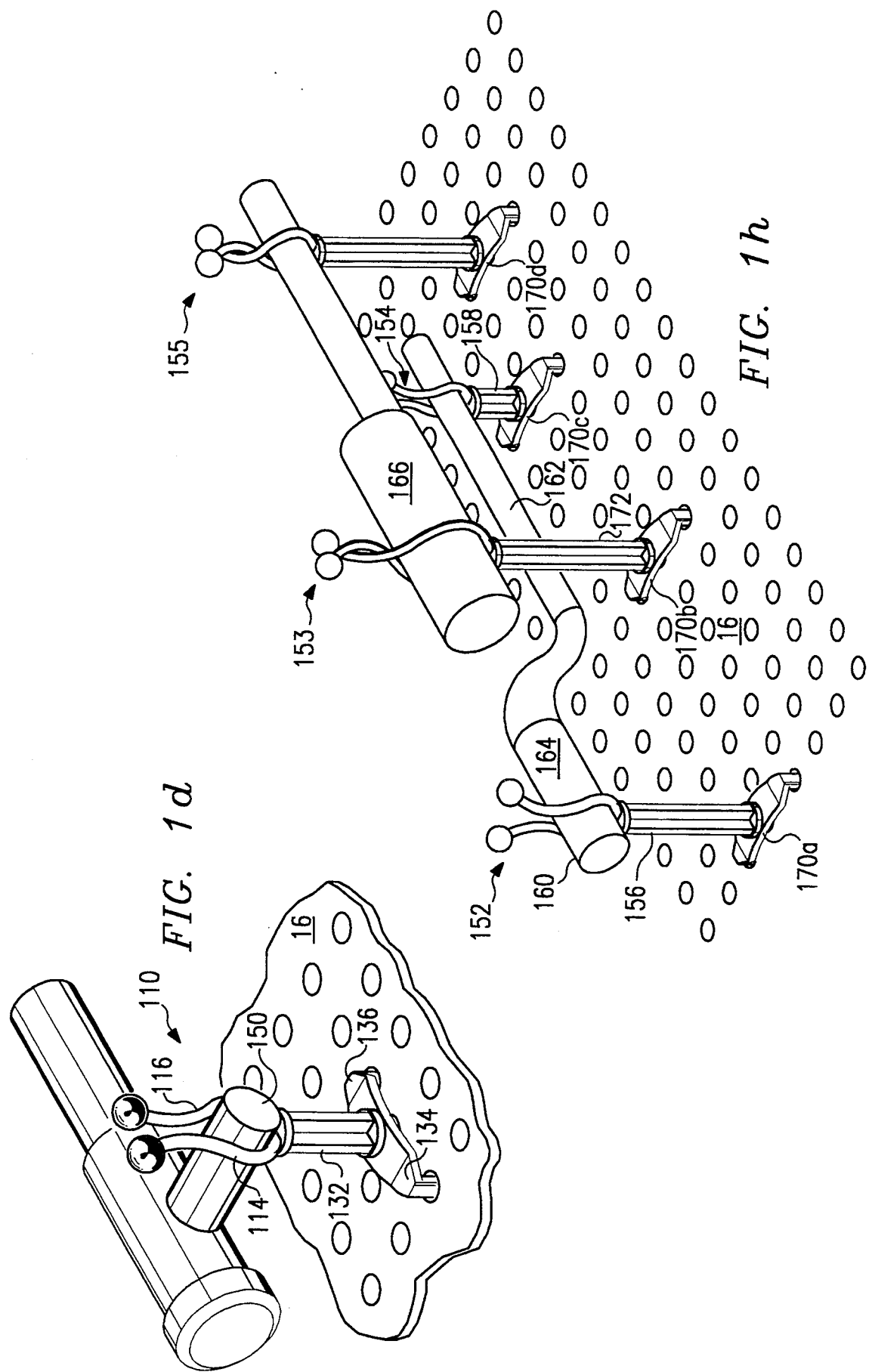

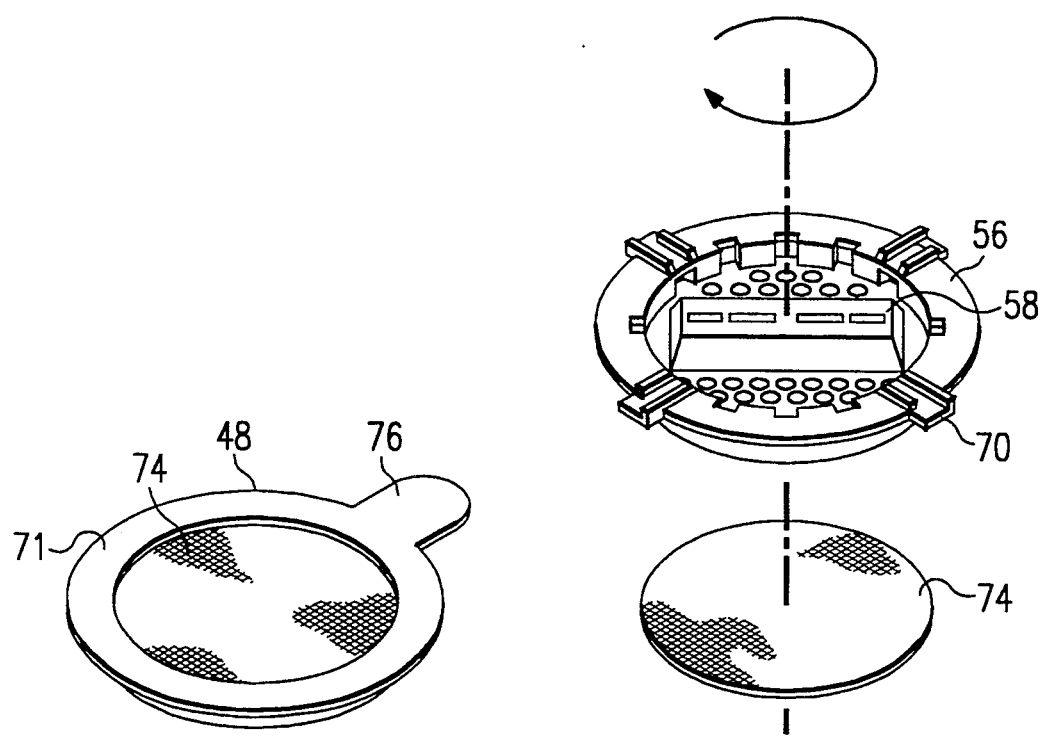
FIG. 14B
FIG. 14A
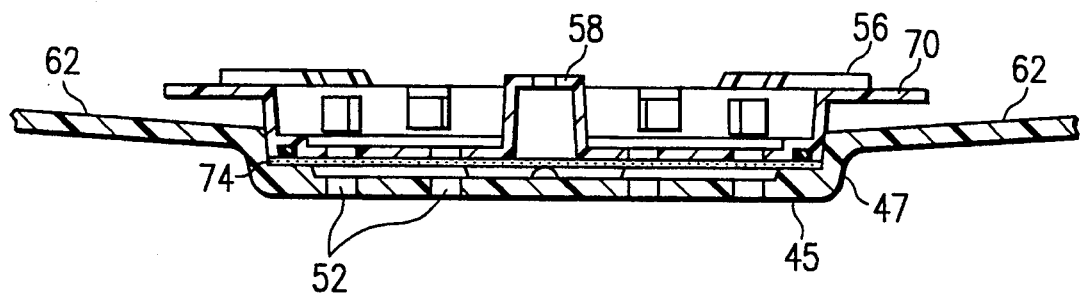
FIG. 15

APPARATUS AND METHOD FOR HOLDING A MEDICAL INSTRUMENT

TECHNICAL FIELD OF THE INVENTION

This invention relates in general to medical instrument containers and in particular to a method and apparatus for holding a medical instrument.

BACKGROUND OF THE INVENTION

Since the time Louis Pasteur discovered the germ theory of infection, medical instruments have required sterilization to prevent contamination and the spread of infection in patients. Hospitals and other medical care providers, faced with substantial numbers of instruments to be sterilized, continually search for techniques to increase the efficiency and speed of sterilization. Moreover, it is difficult for hospitals to accurately determine exactly when medical instruments will be used. Accordingly, after medical instruments have been sterilized, hospitals require storage and transportation facilities to protect the medical instruments against physical damage and contamination.

In order to sterilize medical instruments, hospitals typically use sterilizers that apply steam or other sterilizing gases at a specific heat and humidity for a predetermined time. These sterilizers kill pathogenic organisms located on the instruments and on the containers in which the instruments are held. When such containers are removed from the sterilizer, the instruments inside the containers are sterile. In order to keep the instruments sterile, some previous techniques wrap the instruments in cotton muslin fabric or a non-woven polyolefin material. The instrument wrap protects the instruments against bacteria, dirt, dust and other contaminants so that the instruments are sterile when used.

Such wraps have several shortcomings. Significantly, wraps neither protect delicate instruments from physical damage during handling nor protect health care workers from sharp items wrapped inside. Also, wraps require extra labor in wrapping the instruments. Further, wraps are susceptible to contamination and do not provide for a long shelf-life. Moreover, if wraps are made of cotton material, then the wraps must be washed and processed, thereby adding extra cost. If wraps are made of non-woven disposable materials, then excess waste is created when the wraps are discarded.

Due to the significant shortcomings of instrument wraps, rigid sterilization containers have been developed to hold medical instruments. In expediting the sterilization of medical instruments, hospitals prefer to vertically stack multiple sterilization containers inside a sterilizer. Typically, a rigid tray holds several medical instruments inside the sterilization container. Such a tray normally includes an array of apertures to allow the passage of gases and condensate. Usually, the tray is removable from the rigid sterilization container.

Many medical instruments are very expensive and require special care during physical handling and transportation. If a medical instrument's physical size fails to occupy a sufficiently large amount of available space within the tray, then movement of the tray can result in collisions between the medical instrument and another object such as the tray, the sterilization container, or another medical instrument. Collisions might also occur between two or more medical instruments if the medical instruments are positioned too closely within the tray. Such collisions can extensively damage one or more medical instruments in the tray. Accordingly, the positioning and organization of medical instruments within the tray is especially important for minimizing the risks of physical damage to medical instruments during storage, handling and transportation of sterilization containers. The relative positioning and organization of medical instruments within the tray depends upon each instrument's physical design and its freedom of movement within the tray.

According to some previous techniques for holding medical instruments, silicone rubber blocks are custom manufactured into predefined shapes. These silicone rubber blocks are inserted into the tray to hold medical instruments. Nevertheless, silicone rubber blocks have several shortcomings.

For example, silicone rubber blocks are dedicated to hold only specific types of medical instrument sets that have shapes compatible with a silicone rubber block's predefined shape. Accordingly, silicone rubber blocks impose restrictions that limit their ability to be reconfigured and customized by the user to securely hold a variety of different instrument sets. Moreover, silicone rubber blocks can be obtrusive, and in many cases the area of a medical instrument that contacts a silicone rubber block is inadequately sterilized. Further, silicone rubber blocks are frequently cost prohibitive.

According to other previous techniques for holding medical instruments, stainless steel is formed into predefined shapes. In one such technique, stainless steel is formed into a spring clip and bolted into the tray. A medical instrument is snapped into place between two prongs of the stainless steel spring clip. In another such technique, stainless steel is formed into a rack somewhat analogous in theory to a bicycle rack. Medical instruments are parked in respective slots of the stainless steel rack.

Formed stainless steel has some of the same shortcomings as silicone rubber blocks. For example, formed stainless steel is dedicated to hold only specific types of medical instrument sets that have shapes compatible with the formed stainless steel's predefined shape. Accordingly, formed stainless steel imposes restrictions that limit its ability to be reconfigured and customized by the user to securely hold a variety of different instrument sets. Due to the surface hardness of such steel holders, delicate edges on cutting instruments can get nicked and dulled. Further, formed stainless steel is frequently cost prohibitive.

Thus, a need has arisen for a method and apparatus for holding a medical instrument, in which an adequate separation is maintained between the medical instrument and another object. Also, a need has arisen for a method and apparatus for holding a medical instrument, in which efficiency is increased. Further, a need has arisen for a method and apparatus for holding a medical instrument, in which the risk of physical damage to the medical instrument is reduced during storage, transportation and handling. Moreover, a need has arisen for a method and apparatus for holding a medical instrument, in which a variety of different instrument sets can be securely held, and in which an arrangement of instruments can be reconfigured and customized by the user if desired. Finally, a need has arisen for a method and apparatus for holding a medical instrument, in which the medical instrument is securely held in a more cost effective and less obtrusive manner, and in which more areas of a medical instrument are adequately sterilized.

SUMMARY OF THE INVENTION

In a first aspect of a method and apparatus for holding a medical instrument, the medical instrument is held in a cradle having first and second interlockable regions. The cradle is coupled to a first mating element. The first mating element is coupled to a second mating element through a selected aperture of a platform, such that the cradle is coupled to the platform. The platform has multiple apertures.

In a second aspect of a method and apparatus for holding a medical instrument, the medical instrument is held in a cradle coupled to a first distal end of an elongated body. A second distal end of the elongated body is coupled to a first mating element. The first mating element is coupled to a second mating element through a selected aperture of a platform, such that the cradle is coupled to the platform.

In a third aspect of a method and apparatus for holding a medical instrument, at least one medical instrument is held in multiple holding devices.

It is a technical advantage of the present invention that an adequate separation is maintained between a medical instrument and another object.

It is another technical advantage of the present invention that efficiency is increased.

It is a further technical advantage of the present invention that the risk of physical damage to a medical instrument is reduced during storage, transportation and handling.

It is yet another technical advantage of the present invention that a variety of different instrument sets can be securely held.

It is yet a further technical advantage of the present invention that an arrangement of instruments can be reconfigured and customized.

In another technical advantage of the present invention, a medical instrument is securely held in a less obtrusive manner.

In a further technical advantage of the present invention, more areas of a medical instrument are adequately sterilized.

It is yet another technical advantage of the present invention that a medical instrument is securely held in a more cost effective manner.

It is an even further technical advantage of the present invention that medical instruments can be placed and secured at various levels and planes in a tray, thereby increasing the utilization of space and equipment.

BRIEF DESCRIPTION OF THE DRAWINGS

For a more complete understanding of the present invention, the objects and advantages thereof, reference is now made to the following descriptions taken in connection with the accompanying drawings in which:

FIG. 1a is a perspective view of one embodiment of a medical instrument sterilization container showing the lid in an exploded position;

FIG. 1b is a frontal view of an exemplary holding device of the preferred embodiment;

FIG. 1c is a cross sectional view of the holding device of FIG. 1b;

FIGS. 1d, 1e, 1f, 1g and 1h are perspective views of exemplary holding devices of the preferred embodiment;

FIG. 2 is a partially sectioned view of one half of the length of the present medical instrument sterilization container shown in FIG. 1a with a front elevation thereof;

FIGS. 14a–b are exploded views of a removable filter used in connection with the preferred embodiment; and FIG. 15 is a sectional view of the removable filter shown in FIGS. 14a–b.

DETAILED DESCRIPTION OF THE INVENTION

Figure 1E:
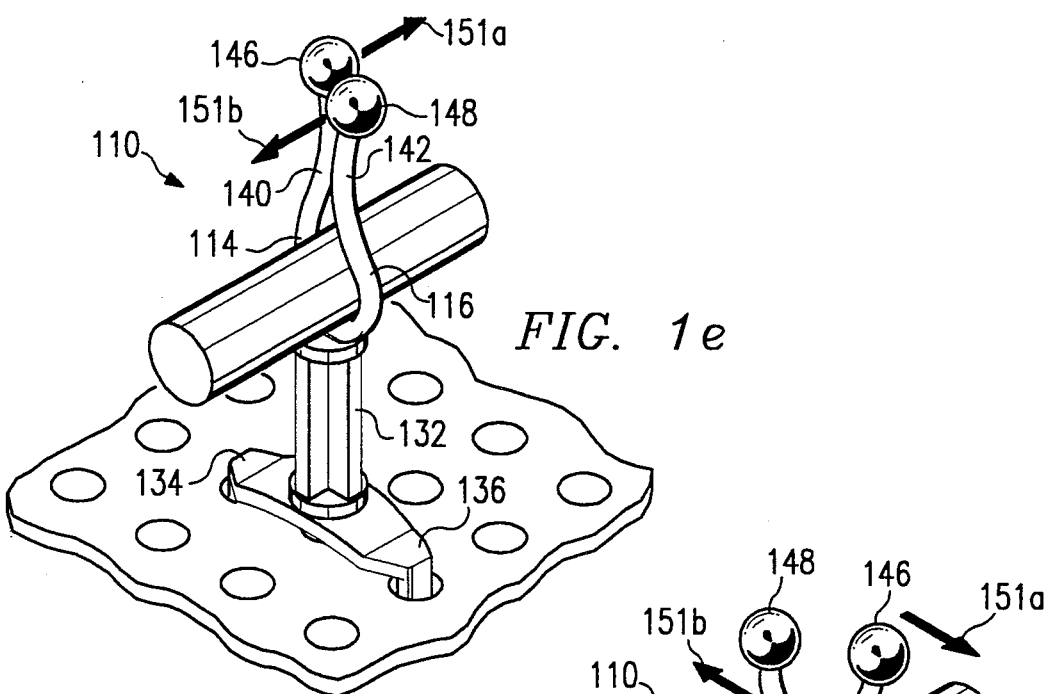

The preferred embodiment of the present invention and its advantages are best understood by referring to FIGS. 1a through 15 of the drawings, like numerals being used for like and corresponding parts of the various drawings.

Referring to FIG. 1a, the present medical instrument sterilization container is identified generally by the numeral 10 and may be seen to include the housing 12 and the removable lid 14. A removable tray 16 sits within the housing 12 and is adapted to receive various medical instruments such as scopes, clamps, forceps, scissors and the like.

An inlet port 18 is disposed on lid 14 in order to allow the passage of sterilizing gases such as steam. Inlet port 18 has beneath it a filter which allows steam and sterilizing gases to pass through during the sterilization process but when dry, prevents or inhibits the passage of bacteria and other contaminants into the interior of the container. Inlet port 18 is elevated above lid surface 19 so that water or moisture generated during the sterilization process is discouraged from entering container 10. Two additional filters, to be subsequently described, are disposed in the bottom of housing 12. The tray 16 includes removable metal handles 20 and 22 to enable easy withdrawal of the tray 16 from the housing 12. Apertures 24 are disposed through the tray 16 to allow the passage of steam and condensate. Metal clamps 26 are attached on both sides of the housing 12 and are manually movable in order to clamp against the lid 14 to secure the lid to secure the housing. Suitable sealing surfaces are provided between the housing 12 and the lid 14 in order to provide an essentially sealed container when the lid is clamped to the housing. Handles 28 are provided on opposite ends of container 12 to facilitate handling.

FIG. 1b shows a holding device indicated generally at 110. Holding device 110 includes a cradle indicated by dashed enclosure 112 for holding a medical instrument. Cradle 112 has first and second interlockable regions 114 and 116. Cradle 112 is connected to a first distal end 118 of an elongated body indicated by dashed enclosure 120. A second distal end 122 of elongated body 120 is connected to a first mating element 124. First mating element 124 is selectively coupled to a second mating element 126 through a selected aperture 128 of tray 16, such that cradle 112 is coupled to tray 16.

Together, first mating element 124 and second mating element 126 form a male-female snap where first mating element 124 is the male element and second mating element 126 is the female element. Cradle 112 can be decoupled from aperture 128 of tray 16 by disconnecting second mating element 126 from first mating element 124. Cradle 112 can then be recoupled to tray 16 by reconnecting second mating element 126 to first mating element 124 through an alternative aperture such as aperture 130.

Elongated body 120 includes a shaft 132 having an X-shaped cross section, as shown in FIG. 1c from the perspective indicated in FIG. 1b. The X-shaped cross section of shaft 132 provides structural reinforcement and support for holding device 110. Other suitable cross sectional shapes can be used in alternative embodiments. Elongated body 120 has a predetermined length. In an alternative embodiment, the length of elongated body 120 can be adjustably lengthened and shortened to vary a distance between cradle 112 and tray 16. In the preferred embodiment, holding device 110 can be formed of a plastic material such as acetal or delrin. Alternatively, holding device 110 can be formed of other materials such as metal or other plastics.

Lateral elements 134 and 136 are coupled through elongated body 120 to cradle 112. Lateral elements 134 and 136 are inserted into additional apertures 130 and 138 to limit movement of cradle 112, particularly rotational movement. Further, lateral elements 134 and 136 stabilize cradle 112 to maintain cradle 112 beyond a minimum distance away from tray 16. Advantageously, even after lateral elements 134 and 136 are inserted into additional apertures 130 and 138, additional apertures 130 and 138 allow passage of gases and condensate through tray 16. Accordingly, apertures of tray 16 are only minimally obscured by holding device 110.

First and second interlockable regions 114 and 116 respectively include first and second curved end regions 140 and 142. First and second curved end regions 140 and 142 respectively include first and second beads 146 and 148. Referring to FIG. 1d, first and second interlockable regions 114 and 116 hold medical instrument 150 by squeezing medical instrument 150 even if first and second interlockable regions 114 and 116 are unlocked.

Figure 1F:
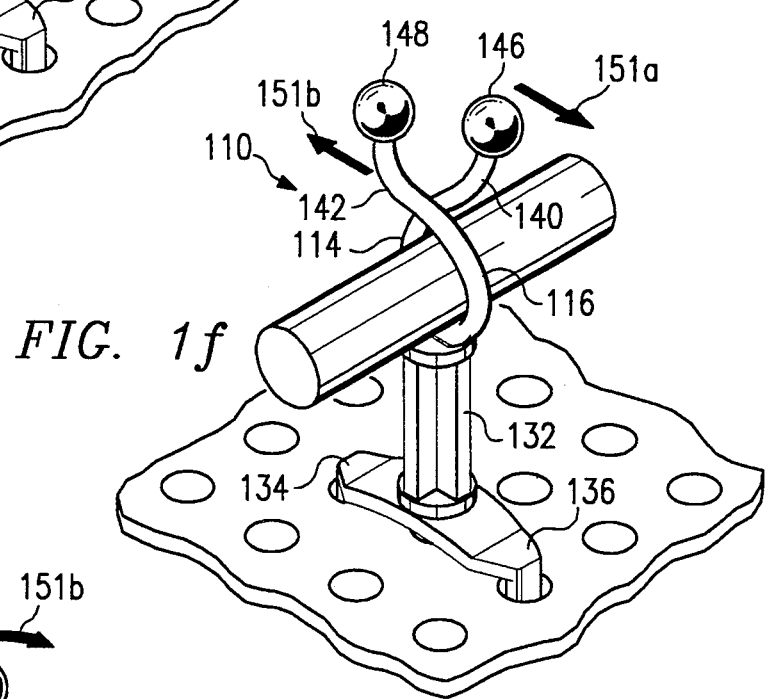
Figure 1G:
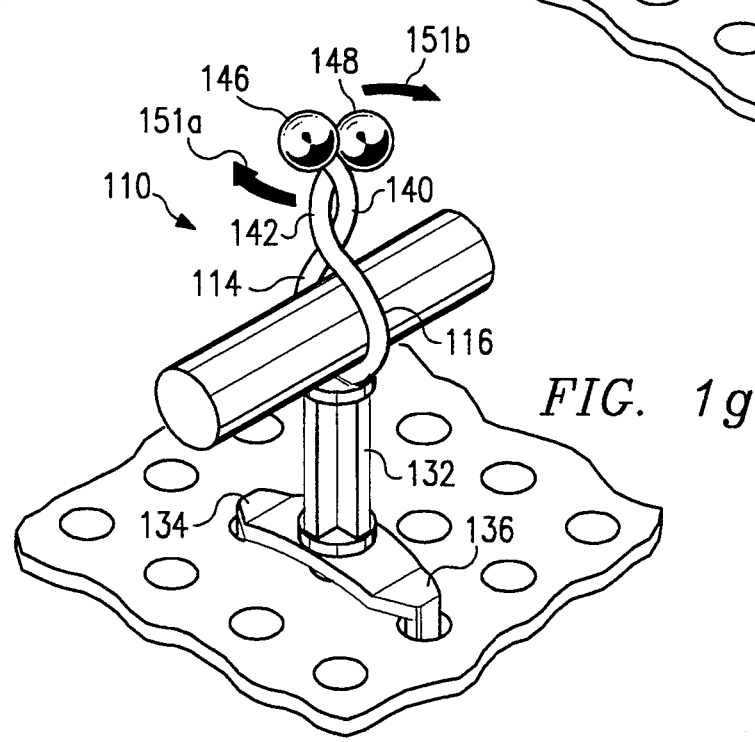

Referring to FIGS. 1e, 1f and 1g, first and second interlockable regions 114 and 116 are interlocked by hooking first curved end region 140 to second curved end region 142, so that holding device 110 holds medical instrument 150 by completely circumscribing medical instrument 150. Advantageously, medical instrument 150 is more securely held when holding device 110 squeezes medical instrument 150 while also completely circumscribing medical instrument 150 as shown in FIG. 1g.

Referring to FIG. 1e, the process of hooking first curved end region 140 to second curved end region 142 can be initiated by moving first bead 146 in a general direction indicated by arrow 151a and by moving second bead 148 in an opposite general direction indicated by arrow 151b. After moving first and second beads 146 and 148 as shown in FIG. 1e, the hooking process continues by moving first and second beads 146 and 148 in the general directions indicated in FIG. 1f by arrows 151a and 151b, respectively. Finally, the hooking process is completed by moving first and second beads 146 and 148 in the general directions indicated in FIG. 1g by arrows 151a and 151b, respectively. After the hooking process is completed as shown in FIG. 1g, first and second beads 146 and 148 engageably contact to more securely maintain first curved end region 140 hooked to second curved end region 142.

As indicated by the changing directions of arrows 151a and 151b between FIGS. 1e, 1f and 1g, the process of hooking first curved end region 140 to second curved end region 142 essentially involves a twisting motion of first and second curved end regions 140 and 142. Advantageously, lateral elements 134 and 136 limit rotational movement of shaft 132 during such a twisting motion. Moreover, first and second interlockable regions 114 and 116 of holding device 110 are selectively interlockable, such that medical instrument 150 is removable from holding device 110 when first and second curved end regions 140 and 142 are unhooked by reversing the twisting motion of FIGS. 1e, 1f and 1g.

The freedom of movement of medical instrument 150 within tray 16 is limited by various elements of holding device 110, including interlockable regions 114 and 116, lateral elements 134 and 136, and mating elements 124 and 126 (shown in FIG. 1b). Since holding device 110 limits the freedom of movement of medical instrument 150 within tray 16, movement of tray 16 is less likely to result in collisions between medical instrument 150 and another object such as tray 16, sterilization container 10, or another medical instrument. Thus, the risk of physical damage to medical instrument 150 is reduced during storage, transportation and handling.

Notably, medical instrument 150 is securely held without requiring a physical size of medical instrument 150 to occupy a substantial amount of available space within tray 16. Moreover, it is unnecessary for holding device 110 to occupy a substantial amount of available space within tray 16 or to substantially obstruct multiple apertures of tray 16. Advantageously, only a slight area of medical instrument 150 is obscured by contact with holding device 110. Accordingly, sterilization container 10 thoroughly and adequately sterilizes medical instrument 150.

A single holding device 110 can be used to hold an associated medical instrument, such as medical instrument 150. Moreover, multiple holding devices, such as holding devices 152, 153, 154 and 155 of FIG. 1f, can be variously combined for particular applications to securely hold different types of medical instruments. For example, elongated bodies 156 and 158 of holding devices 152 and 154 have significantly different lengths, such that different sections 160 and 162 of medical instrument 164 are held at different distances away from tray 16. Moreover, cradles of holding devices 152 and 154 have significantly different sizes for holding sections 160 and 162 of medical instrument 164 having different sizes. Accordingly, medical instruments are securely held in a more cost effective manner, because holding devices 152, 153, 154 and 155 can be rearranged to securely hold a variety of different instrument sets without custom manufacturing.

Similarly, holding devices 152, 153, 154 and 155 can hold multiple medical instruments 164 and 166. The most efficient arrangement of medical instruments within tray 16 varies according to the particular combination of medical instruments and each instrument's physical design. Advantageously, multiple holding devices, such as holding devices 152, 153, 154 and 155, can be reconfigured and customized to securely hold various combinations of dissimilar medical instruments, such as medical instruments 164 and 166.

For example, holding devices 152, 153, 154 and 155 can be decoupled from apertures 170a, 170b, 170c and 170d of tray 16 and then recoupled to alternative apertures of tray 16 as desired for a particular combination of medical instruments. Moreover, cradles of holding devices 152, 153, 154 and 155 have significantly different sizes for holding medical instruments 164 and 166 having different sizes. Further, elongated bodies 158 and 172 of holding devices 154 and 153 have significantly different lengths, such that medical instruments 164 and 166 are held at different distances away from tray 16.

By holding medical instruments 164 and 166 at different distances away from tray 16, medical instrument 164 can be partially interposed between tray 16 and medical instrument 166 as shown in FIG. 1f. Since medical instrument 164 is partially interposed between tray 16 and medical instrument 166, medical instruments 164 and 166 are more closely arranged in tray 16. Accordingly, more medical instruments can be securely held in tray 16 while being thoroughly and adequately sterilized. Advantageously, by securely holding more medical instruments in tray 16, cost efficiency and speed of sterilization are increased.

FIG. 2 illustrates a partially-sectioned view of one embodiment of the medical instrument sterilization container shown in FIG. 1a. The inlet port 18 may be seen to include apertures 30 which communicate with the atmosphere. A removable filter 32 is clamped into place by a twistable cap 34. A sealing portion 36 is illustrated between the housing 12 and the lid 14. The clamp 26 may be seen to comprise a stationary portion 38 which is pivotally mounted by a pivot 40 to a pivotal clamp portion 42. Manual depression upon a lip 44 causes clamp 42 to be moved outwardly in order to accept the lid 14. When the lid 14 is in place, the movable clamp member 42 is moved by spring pressure to clamp against the lid in order to sealingly fix it to the housing.

FIG. 2 further illustrates pedestals 46 which elevate the bottom 45 of the housing 12. Also disposed on the bottom of the housing 12 are two outlet ports or drains 47 and 49. Contained within each of the outlet ports or drains 45 and 49 are disposed filters 48 and 50 which are constructed in a manner similar to filter 32 and in the preferred embodiment they are of the same construction. Apertures 52 are disposed through the bottom 45 of housing 12 in outlet port 47 to permit the passage of sterilizing gases and the removal of condensate. The filter 48 is held in position by twistable cap 56. A handle 58 is provided on the cap 56 to enable twisting into place. Catch members 60 inwardly extend from the bottom of the housing 12 for abutting with portions of the cap 56 in order to maintain the filter 48 securely in place.

Notably, the bottom of housing 12 slopes downwardly toward filtered outlet ports 47 and 49. Specifically, the bottom walls 62 and 64 each slope toward the location of drain 47 in different directions. Thus, condensate or moisture in the left-hand side of the tray of the housing 12 will move by gravity to the drain 47. Likewise, moisture and condensate in the right hand side of the housing 12 will move by gravity along similarly sloping housing bottom wall (not shown) to filter drain 49 (not shown).

Referring again to FIG. 2, tray 16 includes apertures 24 as previously noted. Notably, the tray bottom is configured with domes 66 and apertures 24. This domed configuration causes condensate, steam and the like, to run into the apertures 24 and prevent the accumulation of droplets of condensate or moisture on the bottom of the tray 16.

Figure 3:
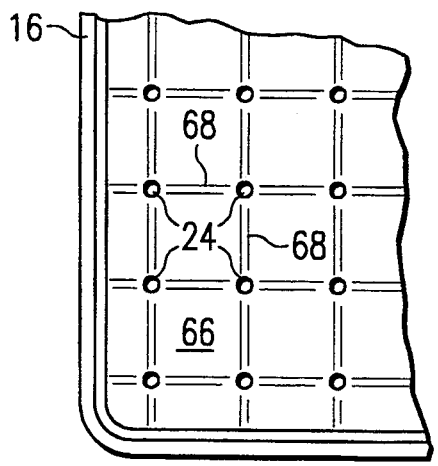
FIG. 3 is a top sectional view of a portion of the bottom of the removable tray taken along section lines 3—3 in FIG. 2.
Figure 5:
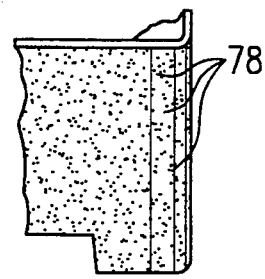
FIG. 5 is a partial view of the housing showing the mixture of high thermal conductivity material with the clear plastic.

Referring to FIG. 3, which illustrates a section of one corner of a tray 16 taken along section lines 3—3 in FIG. 2, domed portions 66 shown from a top view comprise a rectangle with an aperture 24 located at the corner thereof. The domes 66 are formed such that they slope at the corners thereof to an aperture 24. Channels 68 are formed between adjacent apertures 24 to further assist in draining condensate or moisture through the apertures 24.

Figure 4:
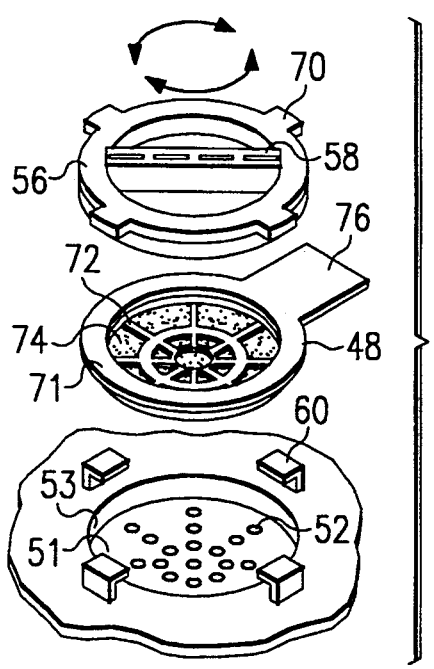
FIG. 4 is an exploded view of one of the removable filters for use in connection with the medical instrument sterilization container of the preferred embodiment.

FIG. 4 illustrates in greater detail the construction of each of the filters 32, 48 and 50 and the manner of securing the filter in the inlet and outlet ports. A twistable cap 56 includes four locking flanges 70. The filters 32, 48 and 50 are circular in shape and include a plastic member 71 having plastic cross-members 72 which support the filter media 74. The filter media 74 may be any suitable type of commercially available filter which allows the passage of sterilizing gases, air and steam therethrough but which prevents or inhibits the passage of contaminants such as dirt, dust and bacteria. Examples of available filter media include those produced and marketed by Dexter. A tab 76 extends from the filter to enable manual insertion or removal of the filter. Filters 32, 48 and 50 are disposable such that they may be periodically replaced. Four locking members 60 are formed around the periphery of each port 18, 47 and 49 for receiving the filters 32, 48 and 50 and a twistable cap 56. In operation, the filters 32, 48 or 50 are placed adjacent to the cover 51 of a selected port 18, 47 or 49 and the cap 56 is twisted such that the locking flanges 70 are tightly held within the locking members 60.

In the preferred embodiment, the present container is formed from a suitable plastic or polymer. As previously noted, clear or translucent plastic, has a low thermal conductivity and cannot absorb enough radiant heat to eliminate condensate within the housing during the drying cycle of the sterilizer system in an economical amount of time. Consequently, the preferred embodiment contemplates the use of additional high thermal conductivity materials in conjunction with non-filled or clear plastic in order to absorb sufficient radiant heat and subsequently rapidly radiate that heat through the container to eliminate condensate in an economical time frame. The preferred embodiment contemplates the mixture of high thermal conductivity materials 78 shown in FIG. 5 within the clear or translucent plastic. Alternatively, a coating of high thermal conductivity materials can be added to the clear or translucent plastic. It will be understood that various types of high thermal conductivity materials may be utilized to accomplish the object of the preferred embodiment. The following are examples which have been found to work well in practice and which provide a sterilization container having a resultant high thermal conductivity which tends to elimination of the formation of condensate when used in a steam sterilizer.

EXAMPLE 1

A plastic is formed for use in a conventional plastic forming machine to provide the present container by charging a non-fluxing type high intensity mixer with polypropylene copolymer, calcium carbonate and low molecular weight polyethylene and mixing to 105 degrees Centigrade. Aluminum flakes are then added and mixed for 15-20 seconds. The mixture is then fed to a single screw compounding extruder and is melt mixed at a temperature of 190 degrees to 205 degrees Centigrade. The resulting polymer is then pelletized as it comes out of the extruder. The resulting copolymer pellets may be utilized in a conventional forming machine to form the present container. The formula for use with this example is listed below as a percentage by weight:

Polypropylene copolymer 55-65% approximately
Aluminum flake 35-50% approximately
Low molecular weight polyethylene 1-5% approximately
Calcium carbonate (CaCO$_3$) 0-15% approximately The polypropylene copolymer may comprise, for example, the copolymer manufactured by Eastman Company and noted as Tenite. Aluminum flakes may comprise the aluminum flakes manufactured by Transmet Corporation and identified as K-151. Suitable low molecular weight polyethylene is manufactured by Allied Fibers and Plastics Company as AC-9. A suitable source of calcium carbonate is Thompson, Wyman & Company under the trade name Atomite.

EXAMPLE 2

A non-fluxing type high intensity mixture is charged with polysulfone, EBS, CaCO$_3$ and titanate and is mixed to 150 degrees Centigrade. Aluminum flakes are then added and mixed for 15 to 20 seconds. The mixture is then fed to a single screw compounding extruder and is melt mixed to a stock temperature of 250 degrees to 260 degrees Centigrade. The formula for this mixture is listed below as a percentage by weight:

Polysulfone 50-60% approximately;
Aluminum flake with silane surface treatment 25-40% approximately;
(EBS) Ethylenebisstearamide 1-5% approximately;
Neoalkoxy Titanate 0.01-1% approximately;
Calcium Carbonate (CaCO$_3$) 1-15% approximately.

The polysulfone may comprise, for example, polysulfone manufactured by Union Carbide as Udel T-1700. A suitable neoalkoxy titanate is manufactured by Kenrich Petrochemicals under the trade name CAPOW 38/M.

EXAMPLE 3

Figure 6:
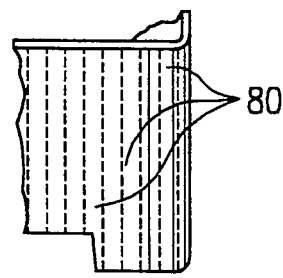
FIG. 6 is a partial view of the housing showing the high conductivity fibers mixed with the plastic.
Figure 7:
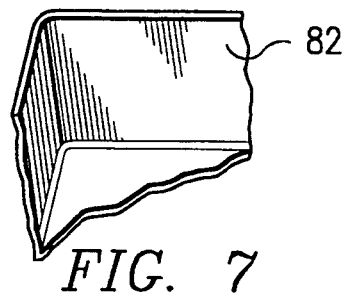
FIG. 7 is a partial view of the housing showing a high thermal conductivity material painted onto the inside surface thereof.

A non-fluxing type high intensity mixture is charged with polysulfone, titanate and EBS and mixed to 150 degrees Centigrade. Carbon fiber 80 shown in FIG. 6, is added and the mixture is mixed to 160 degrees Centigrade. The mixture is then fed to a single-screw compounding extruder and is melt mixed at a stock temperature of 250 degrees to 260 degrees Centigrade.

The formula for this mixture is set forth below as a percentage by weight:

Polysulfone 90% approximately;
Carbon fiber 10% approximately;
Neoalkoxy Titanate 0.01-1% approximately
(EBS) Ethylenebisstearamide 1-5% approximately The carbon fiber may comprise, for example, the fiber manufactured by Union Carbide Specialty Polymers and denoted as Thornel (VMD).

EXAMPLE 4

A clear or translucent plastic container is formed by one of the mixtures noted above such as polypropylene, calcium carbonate and low molecular weight polyethylene. A container is formed by conventional forming techniques and the interior of the housing and lid is then coated with semi-opaque high thermal conductivity material 82 shown in FIG. 7, such as a heat resistant paint or the like which contains carbon or the like. The container may be coated by painting, dipping or other well-known coating techniques. The clear plastic container may alternatively be impregnated with carbon pigments under pressure.

Sterilization containers formed by any of the above examples will have a relatively high thermal conductivity. For example, a thermal conductivity of polysulfone plastic is approximately 1.7 btu/hr/f$^2$/% f/in, while the thermal conductivity of aluminum is 10.8 and carbon fiber is 60 btu/hr/f$^2$/0F/in. Plastic containers formed in accordance with the preferred embodiment absorb substantially more heat through conduction and radiation, and therefore, heat faster and are more effective in moisture evaporation as well as more effective in killing bacteria in marginally operating steam sterilizers. The present container also enables the heat to more rapidly be transmitted to the entire interior, including the tray 16 thereby more effectively treating moisture or bacteria.

Figure 8:
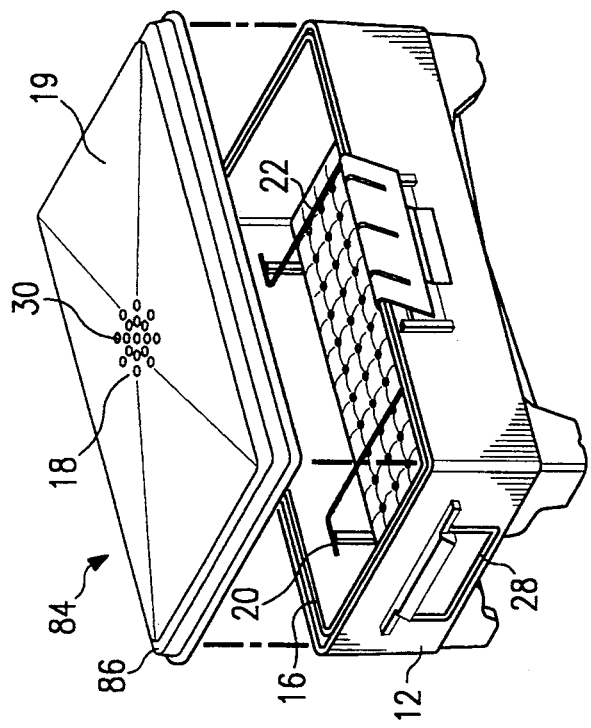
FIG. 8 is a perspective view of an alternative embodiment of a medical instrument sterilization container showing the domed lid in an exploded position.

Referring to FIG. 8, an alternate embodiment of the medical instrument sterilization container of the preferred embodiment is shown generally at 84 and includes housing 12 and a domed removable lid 86. Inlet port 18 is disposed at the apex of the domed lid 86. When container 84 is stacked with a similar container 84 during the sterilization process, the inlet port 18 of the lower container is vertically and laterally spaced from the outlet ports 47 and 49 of the upper container such that steam or condensate exiting the upper container strikes the domed lid away from inlet port 18 of the lower container and is shed to the sides of domed lid 86. This prevents the steam or condensate from flowing into inlet 18 of the lower container of the stack and reduces pooling on the lid surface.

Figure 9:
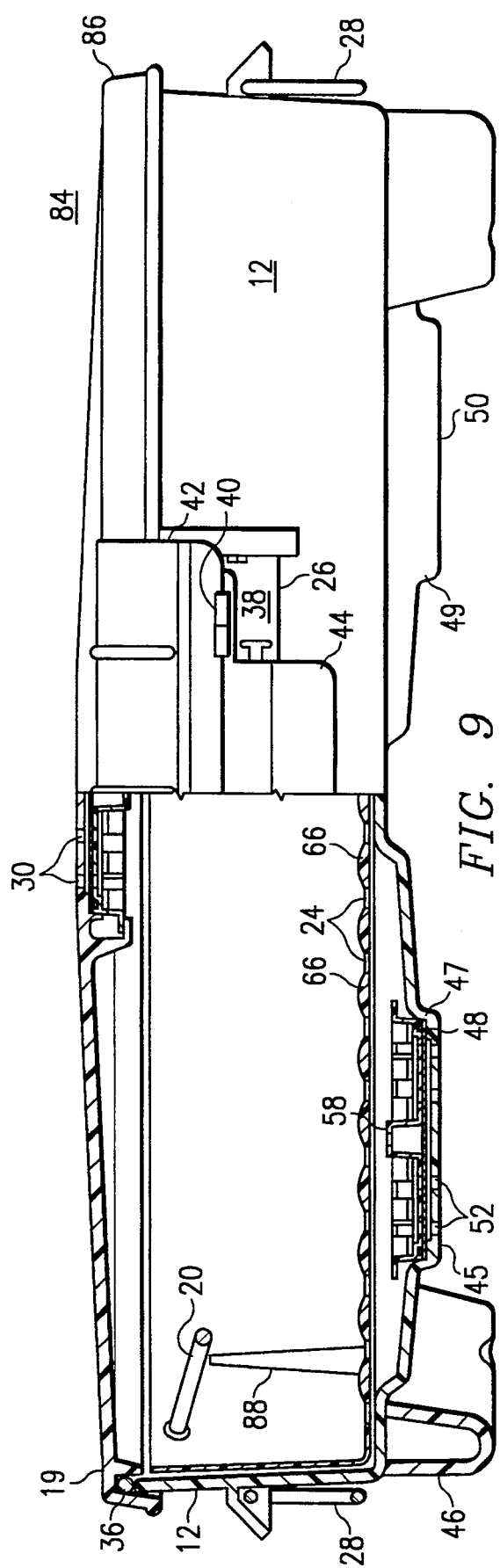
FIG. 9 is a partially sectioned view of one half of the length of the medical instrument sterilization container shown in FIG. 8 taken in connection with a front elevational view.

In the alternate embodiment 84 shown in FIG. 8 and the partially sectioned view of FIG. 9, handles 28 are pivotally mounted to the opposite ends of housing 12 to provide an improved handhold to facilitate manual transport of container 84 while at the same time minimizing space when container 84 is in storage. In a similar fashion, handles 20 and 22 of removable tray 16 are pivotally mounted to the sides of the tray to facilitate withdraw of the tray 16 from the housing 12. As indicated in FIG. 9, stops 88 are provided on the sidewalls of the tray upon which pivotally mounted handles 20 and 22 rest when not in use.

Preferably, the area over which apertures 30 are disposed across the apex of domed lid 86 is less than the respective areas over which apertures 52 are disposed across the bottom surfaces of outlet ports 47 and 49. For example, apertures 30 through lid 86 may be disposed across an area approximately half that of which apertures 52 are disposed across either outlet port 47 or outlet port 49. Such a configuration of the apertures helps expedite the removal of moisture through outlet ports 47 and 49 when a vacuum is applied to the sterilizer chamber by reducing the countervailing upward pressure applied through inlet import 18. A more complete description of this feature is discussed below, With respect to the third embodiment of the present container, which completely eliminates inlet port 18 with respect to inlet port 18.

Figure 10:
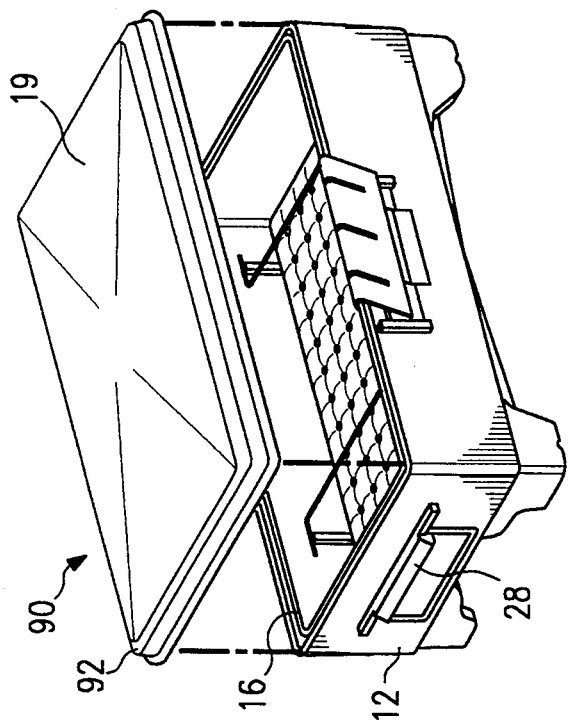
FIG. 10 is another perspective view of the preferred embodiment of the medical instrument sterilization container showing the lid in an exploded position.
Figure 11:
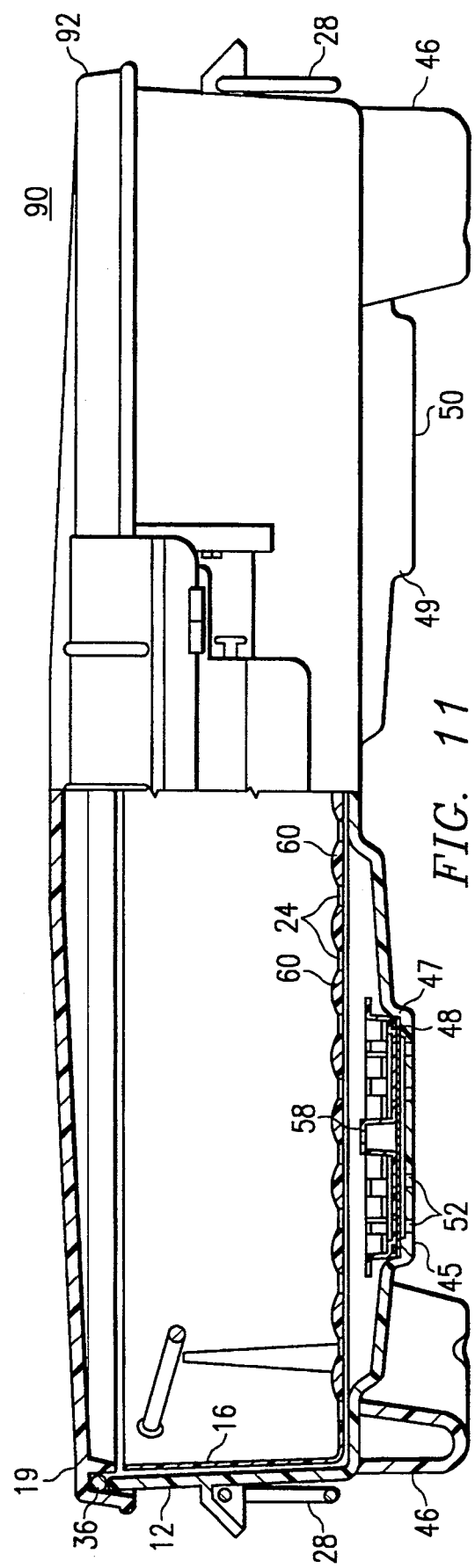
FIG. 11 is a partially sectioned view of one-half of the length of the preferred embodiment shown in FIG. 10 taken in connection with a front elevational view.

Referring next to FIGS. 10 and 11, a third alternate embodiment of the present sterilization container is shown generally at 90. Sterilization container 90 includes an entirely solid domed lid 92 that is in a sealing arrangement to housing 12. In contrast to the embodiment previously described in connection with FIGS. 1-9, sterilization container 90 is not provided with an inlet port 18, hence, no apertures 30 are disposed at the apex of lid 92. When a vacuum is applied to the sterilizer chamber to draw moisture out of container 90, the problem of countervailing forces through an inlet port 32 and the outlet ports 47 and 49 has been eliminated completely.

Figure 12:
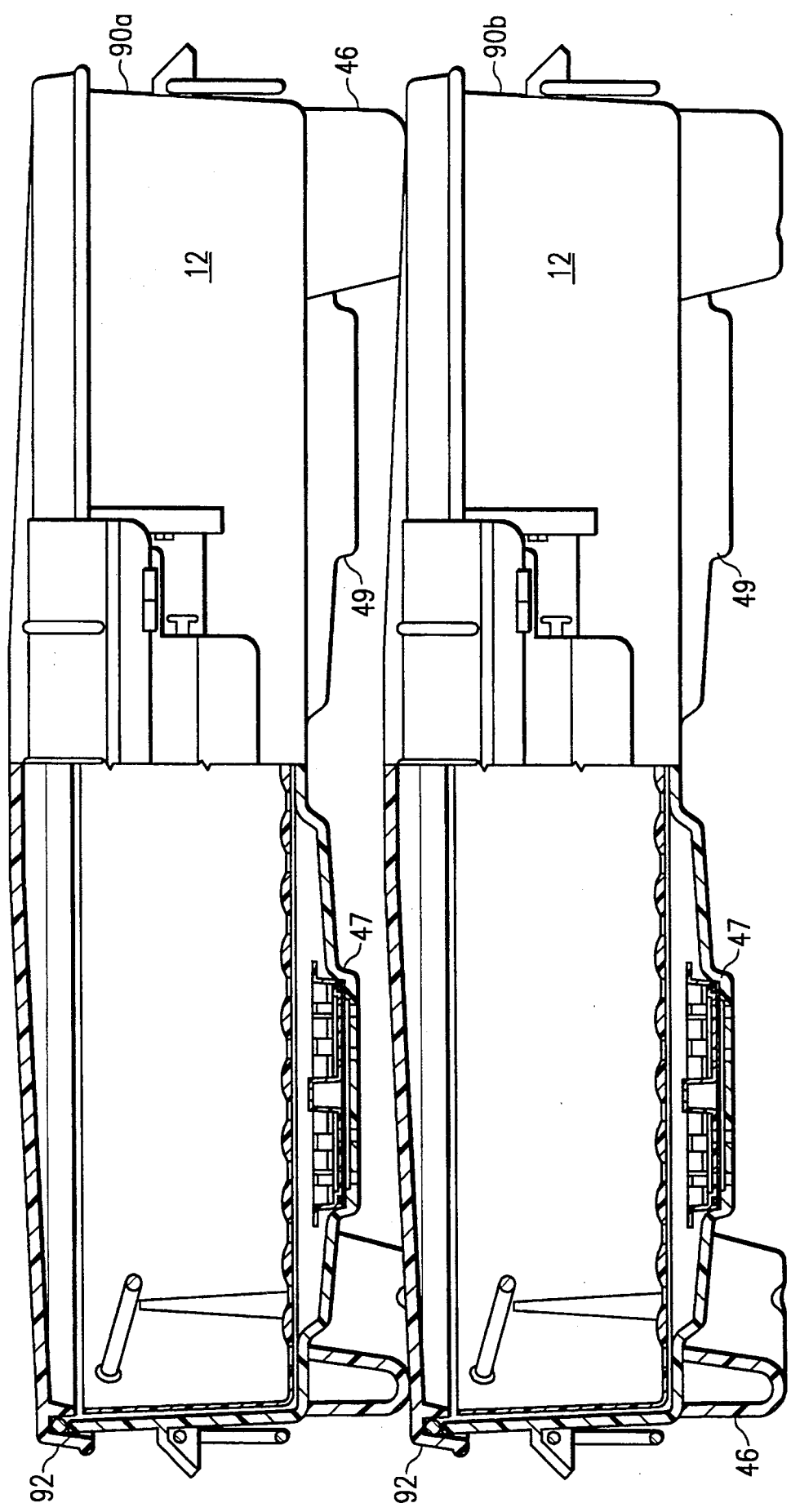
FIG. 12 shows a plurality of the containers described in the preferred embodiment stacked one on top of another.

FIG. 12 depicts a pair of stacked containers 90a and 90b. When stacked, ports 47 and 49 of the upper container are vertically offset and laterally spaced from the apex of domed lid 92 of the lower container. This stacked configuration allows sterilizing steam or gas to flow into and out of ports 47 and 49 without impediment while at the same time providing a structure in which moisture or condensate exiting ports 47 and 49 of the upper container is deflected off the sides of the lid 92 of the lower container to the side and reduces possible pooling of moisture.

Figure 13A:
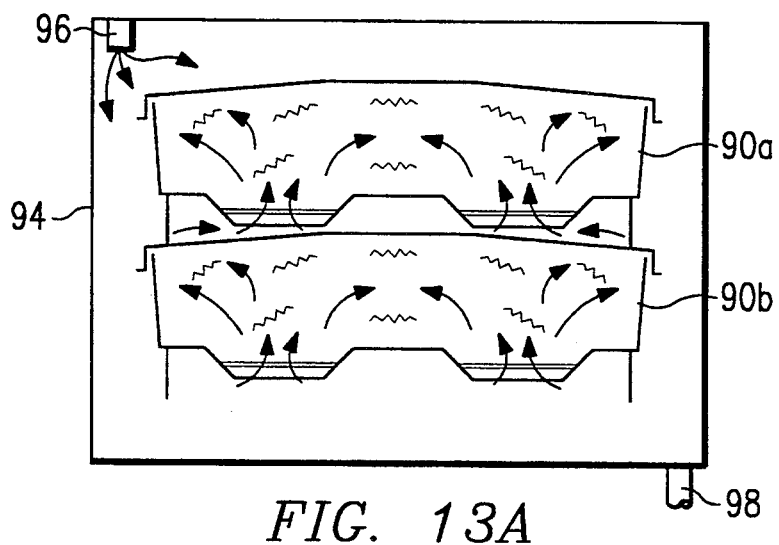
FIGS. 13a, 13b and 13c illustrate the operation of the container of the preferred embodiment in a steam sterilizer.
Figure 13B:
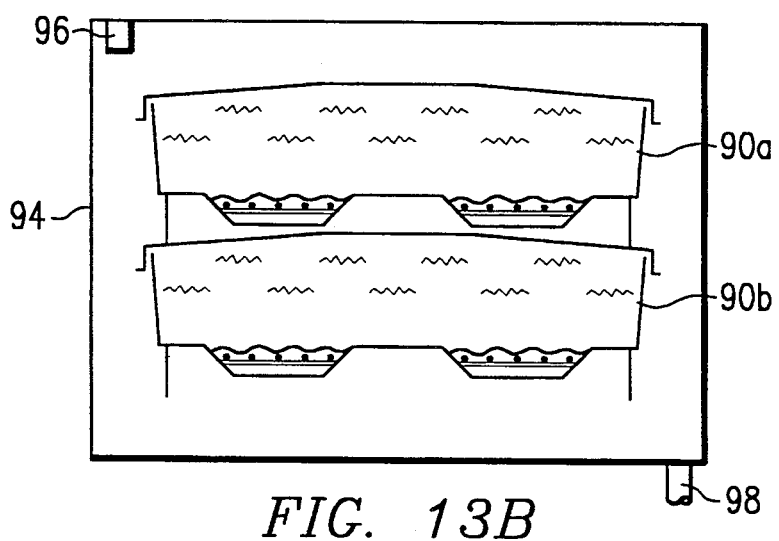
Figure 13C:
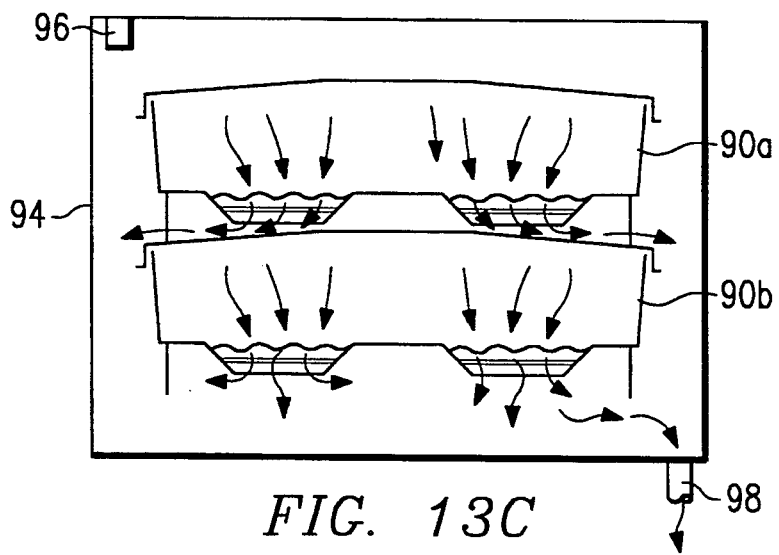

FIGS. 13a through 13c depict the use of a pair of stacked containers 90a and 90b during the sterilization process in a conventional sterilizer 94. In FIG. 13a, steam or sterilizing gas, shown generally by arrows, is injected into the chamber of sterilizer 94 through sterilizer inlet 96. Initially, the pressure in the sterilizer chamber exceeds the pressure inside containers 90a and 90b, providing the requisite pressure differential. The steam or gas then enters through ports 47 and 49 across the filter barriers provided by filters 48 and 50. Pedestals 46 provide the important function of maintaining space between the stacked containers such that the steam can enter ports 47 and 49 without substantial impediment. The steam flowing into the containers 90a and 90b sterilizes the instruments disposed therein. As the steam contacts the instruments inside the containers 90a and 90b and the sidewalls of the housings 12 of containers 90a and 90b condensate is formed.

In FIG. 13b, the pressure inside the sterilization containers 90a and 90b has equalized with the pressure in the chamber of sterilizer 94. Condensate which has formed on the sidewalls of containers 90a and 90b as well as the medical instruments disposed therein, drains to the filtered ports 47 and 49 along the sloped portions of the bottom housing 12. The condensate has a tendency pools on the somewhat hydrophobic barrier created by filters 48 and 50 disposed in respective ports 47 and 49.

Next, as depicted in FIG. 13c, a vacuum is created within the chamber of sterilizer 94. The vacuum withdraws the condensate from containers 90a and 90b by pulling the accumulated condensate across filters 48 and 50 under vacuum pressure. The condensate exits the chamber sterilizer 94 through outlet 98. The removal of condensate across filters 48 and 50 under vacuum pressure allows for a faster and more complete drying of the instruments in the container. The elimination of an inlet port 18 through the lid eliminates countervailing upward pressure on the condensate which impedes rapid withdrawal of the condensate across filters 48 and 50.

FIGS. 14a and 14b depict alternate approaches to filtering ports 18, 47 and 49. In the embodiment shown in FIG. 14a, filter media 74 is directly inserted into the recess of the respective port 18, 47, 49 and subsequently firmly held in place through direct contact with cap 56. A cross-sectional view of the filtering approach using filter media 74 directly inserted into the recess of the respective filter port 18, 47, 49 is shown in FIG. 15. In FIG. 14b, the filter media is again supported in plastic member 71. In this embodiment, however, the filter media 74 is supported such that when the filter 32, 48 or 50 is inserted into the recess or ports 18, 47, 49, filter media 74 is disposed between the inside of the respective container and the cross-members 72. In this configuration, the steam or sterilizing gas exiting the container is not impeded by the cross-members 72 until it has crossed the barrier provided by the filter media 74. This facilitates also more rapid removal of the condensate from the container.

Although the present invention and its advantages have been described in detail, it should be understood that various changes, alterations and substitutions can be made without departing from the spirit and scope of the invention as defined by the appended claims.

What is claimed is:

1. Apparatus for holding a medical instrument, comprising:
    a platform having a plurality of apertures;
    a cradle for holding the medical instrument, said cradle having first and second interlockable regions;
    a first mating element coupled to said cradle; and
    a second mating element for coupling to said first mating element through a selected one of said apertures, such that said cradle is coupled to said platform.

2. The apparatus of claim 1 wherein said first and second interlockable regions are interlocked by hooking said first interlockable region to said second interlockable region.

3. The apparatus of claim 2 wherein at least one of said first and second interlockable regions includes an enlarged region for maintaining said first and second interlockable regions interlocked.

4. The apparatus of claim 1 wherein said first and second interlockable regions respectively include first and second curved end regions.

5. The apparatus of claim 4 wherein said first and second interlockable regions are interlocked by twistably hooking said first curved end region to said second curved end region so that said cradle holds the medical instrument by circumscribing the medical instrument.

6. The apparatus of claim 5 wherein said first and second curved end regions respectively include first and second beads for engageably contacting to maintain said first and second curved end regions interlocked.

7. The apparatus of claim 1 wherein said first and second interlockable regions of said cradle are selectively interlockable, such that the medical instrument is removable from said cradle.

8. The apparatus of claim 1 wherein said cradle holds the medical instrument by squeezing the medical instrument.

9. The apparatus of claim 8 wherein said first and second interlockable regions hold the medical instrument by squeezing the medical instrument while said first and second interlockable regions are unlocked.

10. The apparatus of claim 1 wherein said platform is a tray.

11. The apparatus of claim 1 wherein said first mating element includes a male element of a snap.

12. The apparatus of claim 11 wherein said second mating element includes a female element of said snap.

13. Apparatus for holding a medical instrument, comprising:
a platform having a plurality of apertures;
a cradle having interlockable regions for holding the medical instrument;
an elongated body having first and second distal ends, said first distal end being coupled to said cradle;
a first mating element coupled to said second distal end of said elongated body; and
a second mating element for coupling to said first mating element through a selected one of said apertures, such that said cradle is coupled to said platform.

14. The apparatus of claim 13 wherein said elongated body has a predetermined length.

15. The apparatus of claim 13 wherein said elongated body includes a shaft having an X-shaped cross section.

16. The apparatus of claim 13 wherein said cradle is formed of a plastic material.

17. The apparatus of claim 13 wherein said cradle holds the medical instrument by squeezing the medical instrument.

18. The apparatus of claim 13 and comprising at least one lateral element coupled to said cradle for insertion into at least one additional one of said apertures.

19. The apparatus of claim 18 wherein each said lateral element limits movement of said cradle.

20. The apparatus of claim 18 wherein each said lateral element limits rotational movement of said cradle.

21. The apparatus of claim 18 wherein each said lateral element stabilizes said cradle to maintain said cradle beyond a minimum distance away from said platform.

22. The apparatus of claim 18 wherein each said additional aperture allows passage of condensate through said platform after said lateral element is inserted into said additional aperture.

23. Apparatus for holding at least one medical instrument, comprising:
a platform having a plurality of apertures; and
a plurality of holding devices each comprising:
a cradle having interlockable regions for holding an associated medical instrument;
an elongated body having first and second distal ends, said first distal end being coupled to said cradle;
a first mating element coupled to said second distal end of said elongated body; and
a second mating element for coupling to said first mating element through an associated one of said apertures, such that said cradle is coupled to said platform.

24. The apparatus of claim 23 wherein said plurality of holding devices hold a single medical instrument.

25. The apparatus of claim 24 wherein said elongated bodies of said holding devices have significantly different lengths, such that different sections of said single medical instrument are held at different distances away from said platform.

26. The apparatus of claim 24 wherein said cradles of said holding devices have significantly different sizes for holding sections of said single medical instrument having different sizes.

27. The apparatus of claim 23 wherein said plurality of holding devices hold multiple medical instruments.

28. The apparatus of claim 27 wherein said elongated bodies of said holding devices have significantly different lengths, such that multiple medical instruments are held at different distances away from said platform.

29. The apparatus of claim 28 wherein a first one of said multiple medical instruments is at least partially interposed between said platform and a second one of said multiple medical instruments.

30. The apparatus of claim 27 wherein said cradles of said holding devices have significantly different sizes for holding multiple medical instruments having different sizes.

31. The apparatus of claim 23 wherein said cradle of a selected one of said holding devices is decoupled from said platform by decoupling said second mating element from said first mating element.

32. The apparatus of claim 31 wherein said cradle of said selected holding device is recoupled to said platform by recoupling said second mating element to said first mating element through an alternative one of said apertures.

33. A method of holding a medical instrument, comprising the steps of:
holding the medical instrument in a cradle having first and second interlockable regions, said cradle being coupled to a first mating element; and
coupling said first mating element to a second mating element through a selected aperture of a platform having a plurality of apertures, such that said cradle is coupled to said platform.

34. The method of claim 33 and further comprising the step of interlocking said first and second interlockable regions by hooking said first interlockable region to said second interlockable region.

35. The method of claim 33 and further comprising the step of interlocking said first and second interlockable regions by twistably hooking a first curved end region of said first interlockable region to a second curved end region of said second interlockable region, so that said cradle holds the medical instrument by circumscribing the medical instrument.

36. The method of claim 35 and further comprising the step of engageably contacting first and second beads of said first and second curved end regions, respectively, to maintain said first and second curved end regions interlocked.

37. The method of claim 33 and further comprising the step of selectively interlocking said first and second interlockable regions of said cradle, such that the medical instrument is removable from said cradle.

38. The method of claim 33 wherein said holding step is performed by squeezing the medical instrument in said cradle.

39. The method of claim 38 wherein said holding step is performed by squeezing the medical instrument in said cradle while said first and second interlockable regions are unlocked.

40. A method of holding a medical instrument, comprising the steps of:

holding the medical instrument in a cradle having interlockable regions coupled to a first distal end of an elongated body, a second distal end of said elongated body being coupled to a first mating element; and coupling said first mating element to a second mating element through a selected aperture of a platform having a plurality of apertures, such that said cradle is coupled to said platform.

41. The method of claim 40 wherein said holding step is performed by squeezing the medical instrument in said cradle.

42. The method of claim 40 further comprising the step of inserting at least one lateral element coupled to said cradle into an additional one of said apertures.

43. The method of claim 42 wherein said inserting step is performed by inserting at least one lateral element into an additional one of said apertures, such that each said lateral element limits movement of said cradle.

44. The method of claim 42 wherein said inserting step is performed by inserting at least one lateral element into at least one additional one of said apertures, such that said lateral element stabilizes said cradle to maintain said cradle beyond a minimum distance away from said platform.

45. A method of holding a medical instruments comprising the steps of:

holding at least one medical instrument in a plurality of holding devices each comprising a respective cradle having interlockable regions for holding an associated medical instrument, each said cradle being coupled to a first distal end of a respective elongated body, a second distal end of each said elongated body being coupled to a respective first mating element; and coupling each said first mating element to a respective second mating element through an associated aperture of a platform having a plurality of apertures, such that each said cradle is coupled to said platform.

46. The method of claim 45 wherein said holding step comprises the step of holding a single medical instrument in said plurality of holding devices.

47. The method of claim 46 wherein said holding step comprises the step of holding different sections of said single medical instrument at different distances away from said platform in response to significantly different lengths of said elongated bodies.

48. The method of claim 46 wherein said holding step comprises the step of holding said single medical instrument in said plurality of holding devices, said cradles of said holding devices having significantly different sizes for holding sections of said single medical instrument having different sizes.

49. The method of claim 45 wherein said holding step comprises the step of holding multiple medical instruments in said plurality of holding devices.

50. The method of claim 49 wherein said holding step comprises the step of holding multiple medical instruments at different distances away from said platform in response to significantly different lengths of said elongated bodies.

51. The method of claim 50 wherein said holding step comprises the step of holding multiple medical instruments at different distances away from said platform, such that a first one of said multiple medical instruments is at least partially interposed between said platform and a second one of said multiple medical instruments.

52. The method of claim 49 wherein said holding step comprises the step of holding multiple medical instruments in said plurality of holding devices, said cradles of said holding devices having significantly different sizes for holding multiple medical instruments of different sizes.

53. The method of claim 45 and further comprising the step of decoupling said cradle of a selected one of said holding devices from said platform by decoupling said second mating element from said first mating element.

54. The method of claim 53 and further comprising the step of recoupling said cradle of said selected holding device to said platform by recoupling said second mating element to said first mating element through an alternative one of said apertures.

* * * * *

UNITED STATES PATENT AND TRADEMARK OFFICE
CERTIFICATE OF CORRECTION

PATENT NO. : 5,346,075
DATED : September 13, 1994
INVENTOR(S) : Nichols, et al

It is certified that error appears in the above-indentified patent and that said Letters Patent is hereby corrected as shown below:

Column 15, line 1 after "medical" delete "instruments" and insert -- instrument --.

Signed and Sealed this

Twenty-first Day of February, 1995

Attest:

BRUCE LEHMAN

Attesting Officer        Commissioner of Patents and Trademarks